United States Patent
Janssen et al.

(10) Patent No.: US 10,172,726 B2
(45) Date of Patent: Jan. 8, 2019

(54) ARTIFICIAL LIMB CASING AND METHOD FOR THE PRODUCTION THEREOF

(75) Inventors: Heinz-Gerd Janssen, Duderstadt (DE); Markus Schneegans, Rollshausen (DE); Waldemar Schneegans, Duderstadt (DE)

(73) Assignee: OTTO BOCK HEALTHCARE GMBH, Duderstadt (DE)

( * ) Notice: Subject to any disclaimer, the term of this patent is extended or adjusted under 35 U.S.C. 154(b) by 333 days.

(21) Appl. No.: 13/505,239

(22) PCT Filed: Oct. 5, 2010

(86) PCT No.: PCT/EP2010/006065
§ 371 (c)(1),
(2), (4) Date: Apr. 30, 2012

(87) PCT Pub. No.: WO2011/050894
PCT Pub. Date: May 5, 2011

(65) Prior Publication Data
US 2012/0283846 A1  Nov. 8, 2012

(30) Foreign Application Priority Data
Oct. 30, 2009 (DE) .................. 10 2009 051 441

(51) Int. Cl.
*A61F 2/54* (2006.01)
*A61F 2/60* (2006.01)
(Continued)

(52) U.S. Cl.
CPC .................. *A61F 2/60* (2013.01); *A61F 2/54* (2013.01); *A61F 2/582* (2013.01); *A61F 2/583* (2013.01);
(Continued)

(58) Field of Classification Search
CPC ........... A61F 2002/5001; B25J 19/0075; B25J 19/0083
See application file for complete search history.

(56) References Cited

U.S. PATENT DOCUMENTS 3,953,900 A  5/1976 Thompson
4,007,496 A  2/1977 Glabiszewski
(Continued)

FOREIGN PATENT DOCUMENTS

CN  101478936 A  7/2009
DE  100 40 955 A1 *  3/2002  .............. A61F 2/78
(Continued)

OTHER PUBLICATIONS

Computer generated translation of DE 100 40 955 A1, published on Mar. 7, 2002.*
(Continued)

*Primary Examiner* — David H Willse
(74) *Attorney, Agent, or Firm* — Holland & Hart

(57) ABSTRACT

The invention relates to an artificial limb casing (1) having an insertion opening (4) for inserting the artificial limb, wherein a joint area (3) to which an end area (2) is integrally connected is formed on the casing (1). The invention further relates to a method for producing an artificial limb casing (1), wherein a textile intermediate layer (8) is applied to the outside of a hollow polyurethane substrate (9), and a silicone layer (7) is applied to the textile intermediate layer. The casing (1) is made of an elastomer material that has a lower Shore hardness in the joint area (3) than in the end area (2).

19 Claims, 3 Drawing Sheets

(51) Int. Cl.
*A61F 2/78* (2006.01)
*A61F 2/50* (2006.01)
*A61F 2/58* (2006.01)
*A61F 2/64* (2006.01)
*A61F 2/66* (2006.01)

(52) U.S. Cl.
CPC . *A61F 2/64* (2013.01); *A61F 2/66* (2013.01); *A61F 2002/5001* (2013.01); *A61F 2002/5056* (2013.01)

(56) References Cited

U.S. PATENT DOCUMENTS

| | | | |
|---|---|---|---|
| 4,180,872 A | | 1/1980 | Chaikin |
| 4,846,843 A | | 7/1989 | Gammer |
| 5,133,775 A | | 7/1992 | Chen |
| 5,593,453 A | * | 1/1997 | Ahlert ............... 623/27 |
| 7,438,843 B2 | | 10/2008 | Asgeirsson |
| 7,503,937 B2 | * | 3/2009 | Asgeirsson et al. ............ 623/55 |
| 9,180,027 B2 | | 11/2015 | Kettwig et al. |
| 2006/0015192 A1 | | 1/2006 | Clausen et al. |

FOREIGN PATENT DOCUMENTS

| | | |
|---|---|---|
| DE | 60012937 T2 | 9/2005 |
| DE | 202007009077 U1 | 11/2007 |
| EP | 0281855 A1 | 2/1988 |
| EP | 0985388 A2 | 3/2000 |
| EP | 2002806 A2 | 12/2008 |
| GB | 2341325 A | 3/2000 |
| GB | 2357725 A | 4/2001 |
| WO | 0051537 A1 | 9/2000 |
| WO | 0167842 A1 | 9/2001 |
| WO | 2005117746 A2 | 12/2005 |
| WO | 2006005569 A2 | 1/2006 |
| WO | 2008044052 A1 | 4/2008 |
| WO | 2009015627 A2 | 2/2009 |
| WO | 2009115835 A1 | 9/2009 |

OTHER PUBLICATIONS

PCT International Search Report for PCT International Patent Application No. PCT/EP2010/006065, dated Jun. 15, 2011.
English Translation of the First Office Action in Chinese Application No. 2014106434659, dated Mar. 30, 2016.

* cited by examiner

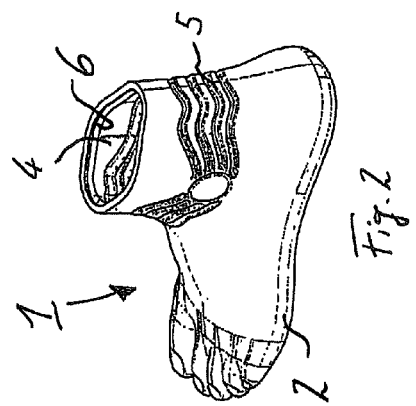
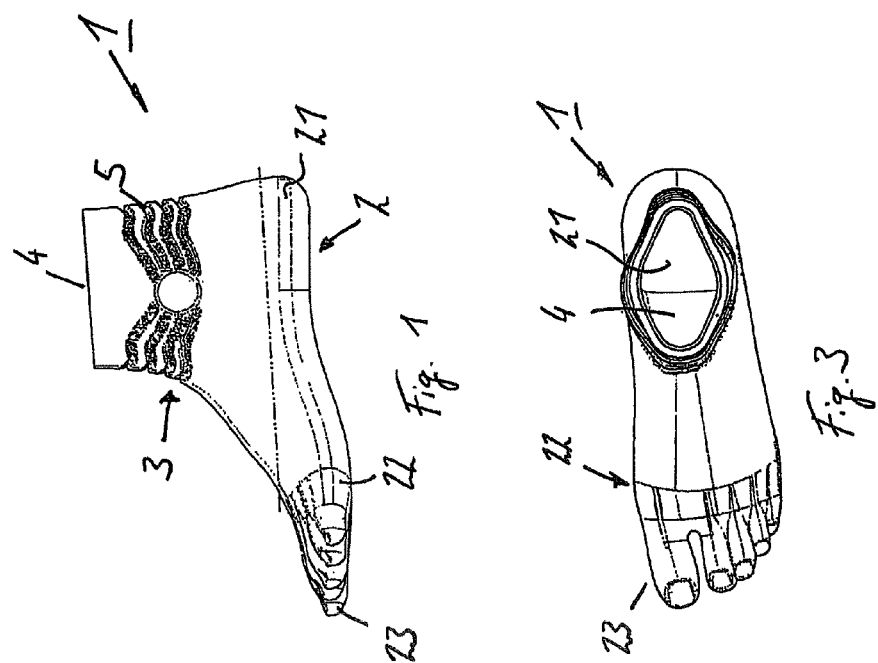

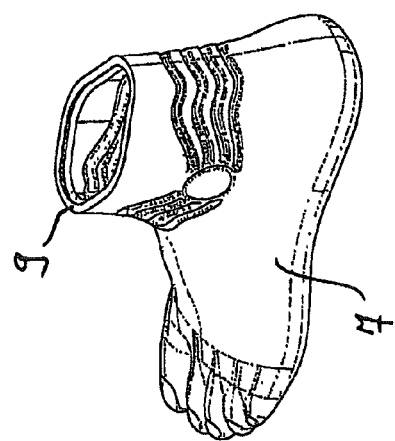
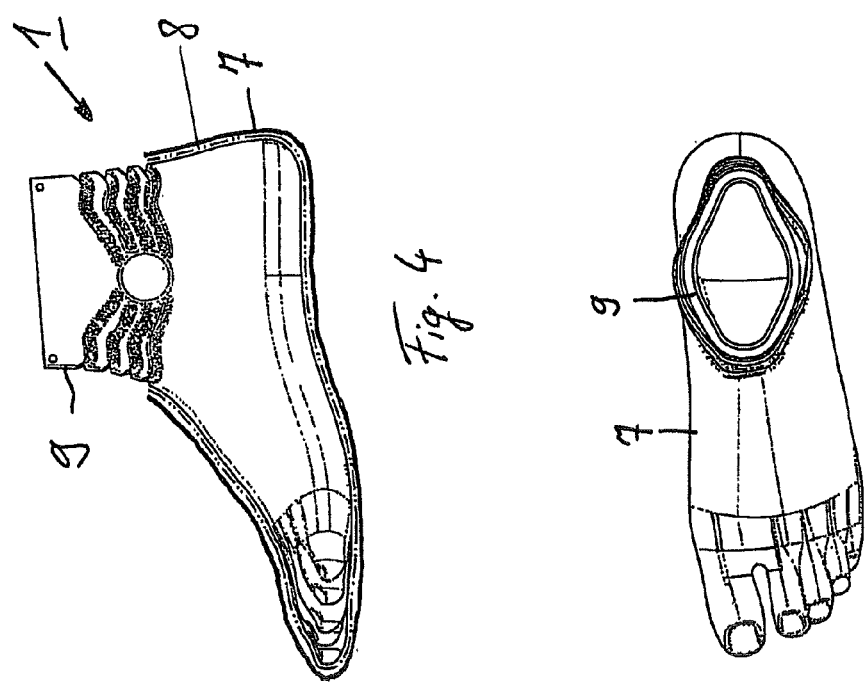
Fig. 4

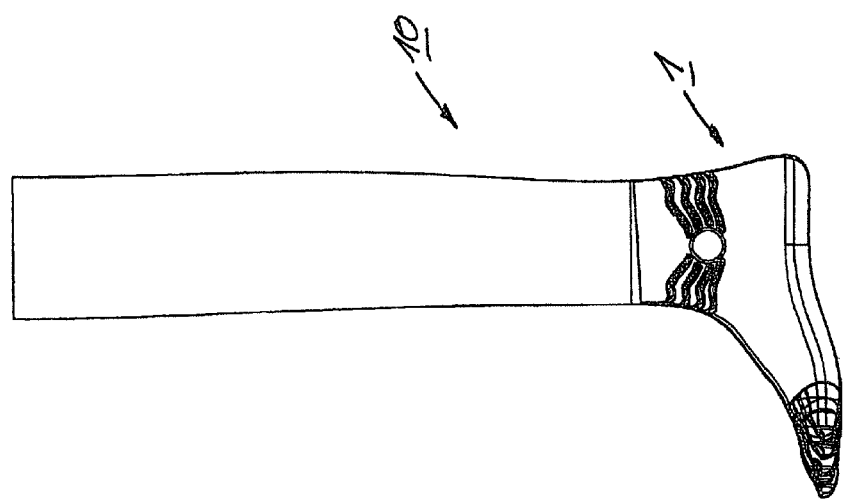

ARTIFICIAL LIMB CASING AND METHOD FOR THE PRODUCTION THEREOF

The invention relates to an artificial limb casing for an artificial limb, for example for a prosthetic foot or a prosthetic hand, having an insertion opening for inserting the artificial limb, wherein a joint area to which an end area is integrally connected is formed on the artificial limb casing. The invention likewise relates to a method for producing an artificial limb casing.

Prostheses are used to replace missing limbs of a body. The main task of the prosthesis here is generally to restore the impaired or lost function. Apart from the purely functional component, visual or cosmetic functions are also fulfilled by the replacement of the lost limbs. For this purpose, it is provided that the functional core of the prosthesis is surrounded by a covering, which provides an appearance that is as natural as possible, so that it is not noticeable at first glance that a prosthesis is being worn.

Foot prostheses were first worked from a wooden core. Such a wooden core was then surrounded with an adhesively attached water-repellent elastic material to improve the resistance to water. This is described for example in U.S. Pat. No. 4,180,872. The technical configuration of the wooden core was restricted to a purely supporting and rolling function.

A leg prosthesis with a shin-bone area, an upper leg area and a knee-joint area is shown in U.S. Pat. No. 3,953,900. All of the areas are surrounded by separate coverings, the coverings that are adjacent to one another overlapping one another. The prosthetic foot does not have any covering. U.S. Pat. No. 4,007,496 describes a connection between a lower leg casing and a prosthetic foot. Here, too, it is not envisaged that the prosthetic foot has a cosmetic covering.

GB 2 357 725 describes a cosmetic covering of silicone for a leg prosthesis. The cosmetic covering has a hollow foot area and a hollow shin-bone area. The material of the covering can be rolled onto the prosthesis, so that one ready-made size of the covering is sufficient for the prostheses that are usually used. A silicone material with a hardness that is greater than the hardness of the material in the calf area may be used in the shin-bone area. The artificial limb casing is made to match the shape of the shin-bone area. The artificial limb casing may in this case have a hardness that is different from the hardness of the material for the lower-leg area.

GB 2 341 325 describes a method for producing a prosthesis or orthesis covering. In this case, difference colorations are applied in a plurality of layers, in order to obtain an overall appearance that resembles natural skin. The foot part of the covering is made to match the shape of the lower-leg part.

WO 2005/117746 A2 describes a functional artificial limb casing having an opening at the upper end and a cavity for receiving a prosthetic foot. The wall which surrounds the cavity has the shape of a natural human foot and forms, inter alia, a bottom part with a sole area, which has a toe portion, a heel portion and a mid-foot portion. In the sole area, different degrees of stiffness are formed, in order to achieve a desired rolling behavior from the heel to the toe and from the lateral side to the medial side. For this purpose, it is provided for example that inserts are incorporated in the heel area and ball area. Stiff elements may likewise be fastened to the covering.

An object of the present invention is to provide an artificial limb casing that has a high wear resistance, is sufficiently elastic to make sufficient adaptability possible, for example in the case of prosthetic feet with an adjustable heel height, and is additionally of a compact structure, in order to be as inconspicuous as possible. An object is likewise to provide a method for producing such an artificial limb casing.

According to the invention, this object is achieved by an artificial limb casing with the features of claim 1 and the method according to the independent claim. Advantageous configurations and developments of the invention are presented in the dependent claims.

The artificial limb casing according to the invention for an artificial limb, having an insertion opening for inserting the artificial limb, wherein an ankle area to which an end area is integrally connected is formed on the artificial limb casing, provides that the artificial limb casing is formed from an elastomer material, for example a polyurethane material, that has a lower Shore hardness in the joint area, in the case of a prosthetic foot casing in particular in the ankle area, than in the end area, in the case of the prosthetic foot casings in the sole area. In the case of prosthetic feet with an adjustable heel height, it is necessary that the ankle area of the artificial limb casing is sufficiently movable to be able to match the varying basic settings of the prosthetic foot. In the case of prosthetic hands, a high degree of mobility and elasticity is necessary on account of the great range of movement and the diverse movement possibilities of the prosthetic hand. Foam materials are therefore usually used for artificial limb casings, but they do not allow the artificial limb to be sealed in the joint area against the ingress of water or dirt. In addition, the foam material is obtrusive and only has a low wear resistance. A configuration of the artificial limb casing made from silicone material is disadvantageous, since the tear propagation resistance is very low in the case of silicone. If a tear forms within the silicone covering, it increases in size very easily. An elastomer material, for example a polyurethane material, which has a much better tear propagation resistance than the silicone materials that are usually used, is therefore provided according to the invention. A problem here, however, is that the elastomer materials, in particular polyurethane materials, only have a low elasticity, in particular if they are designed such that they have a sufficient wear resistance for the highly stressed areas in the heel, on the ball or at the ankles or fingertips. It is therefore provided according to the invention that a much harder elastomer material is used for example in the area of the palm and fingers and in the area of the sole than in the area of the joint, so that the artificial limb casing or artificial limb cosmetic covering is solid and stable in the end area, while a soft and elastic configuration of the elastomer material is present in the area of the insertion opening.

The elastomer material, for example polyurethane material, advantageously has a hardness of 15 to 20 Shore A in the joint area, while the elastomer material has a hardness of 45 to 75 Shore A in the end area, for example in the sole area. In this way it is possible on the one hand to meet the strength and durability requirements of the artificial limb casing and on the other hand to provide the desired elasticity in the area of the insertion opening and in the joint or ankle area.

A further improvement of the elasticity is achieved if a concertina structure is formed in the joint or ankle area. In the case of a prosthetic foot, the ankle area extends both in the proximal direction and in the distal direction of the pivot axis of the prosthetic foot, which generally lies in the area of the ankle of a natural foot. The ankle area of the prosthetic foot casing consequently also extends in the proximal direction, that is to say above the pivot axis of the prosthetic foot. A corresponding configuration can be provided in the case of other artificial limbs, for example in the case of prosthetic hands, in which the joint area is formed in the area of the natural hand joint and extends both in the direction of the mid-hand and in the direction of the lower arm. The concertina structure allows, for example, that the heel height can be set substantially freely and the prosthetic hand can be moved freely. It is likewise possible by way of the concertina structure to reduce material stretching or compression during movement in the artificial limb casing, so that not only easier adjustability but also increased long-term strength of the artificial limb casing are achieved.

It is provided with preference that the elastomer material has a uniform hardness in the end area, in particular in the sole area, in order to obtain a uniform material structure. This avoids separating joints or predetermined breaking points from being formed by material transitions.

A further improvement of the elasticity is achieved by there being a lower material thickness in the joint area than in the end area, wherein material reinforcements may also be provided in particularly stressed areas of the end area. Such material reinforcements are present in particular in the heel area, ball area, toe area, fingertip area and/or palm area. If appropriate, a material reinforcement may be provided in all of these areas. Should it be found on account of the nature of the artificial limb or adapted components that only low material stressing is to be expected at some points, the material reinforcement may also be present only in parts of these areas.

The hardness of the elastomer material may decrease continuously from the end area to the joint area. As an alternative to this, it is provided that different zones of decreasing material hardness are provided from the end area to the joint area. The artificial limb casing consequently has zonings that have different material thicknesses, material hardnesses or else colorations, so that an adaptation of the artificial limb casing to the respective applications can take place.

A development of the invention provides that a sealing ring, in particular what is known as an O-ring, is embedded at the insertion opening of the artificial limb casing, in order to improve the sealing between the artificial limb casing and the artificial limb or between the artificial limb casing and the shaft region of an upper connecting part. This reduces the susceptibility of the artificial limbs to problems, since ingress of water can be effectively prevented.

A silicone coating may be applied on the outer side of the elastomer material, in particular polyurethane material, in order to achieve an improved visual effect and an improved feel, since the silicone coating has a very natural surface.

A further improvement of the invention provides that a textile intermediate layer, in particular a fleece layer, a velour layer or a flock layer, is arranged between the silicone coating and the elastomer material in order to improve the adhesion of the silicone to the elastomer material. Apart from the improved feel as a result of the silicone coating, an improved visual effect would also be achieved, since the silicone coating can be adapted better to the natural appearance. The textile intermediate layer improves the adhesiveness of the silicone to the elastomer material, in particular if the textile intermediate layer is embedded in the elastomer material and the silicone material can enter into an interlocking connection with the part of the textile intermediate layer that is not embedded. The fleece layer or textile intermediate layer may additionally be used to improve the natural look of the artificial limb, in that the coloring of the intermediate layer is adapted to the form of a natural skin surface.

The silicone coating may also be adhesively attached on the covered artificial limb casing. The silicone coating may be separately produced and connected to the textile intermediate layer, for example a fleece layer, by way of adhesive bonding. For this purpose, the textile-covered artificial limb casing is brushed or sprayed with a silicone adhesive or wetted with it in some other way, for example by immersion; the silicone cosmetic covering or the silicone coating is subsequently rolled over or drawn over. Alternatively, the silicone layer or the silicone coating may be applied in a silicone bath. Generally provided as the bonding agent between the textile layer and the silicone coating or the silicone adhesive are liquid silicones, wherein the application of the bonding agent may take place in an immersion bath. The bonding agents enter into an interlocking connection with the textile covering and a material-bonding connection with the silicone coating.

The arrangement of the textile intermediate layer between the substrate material, in particular polyurethane, and the silicone layer is also in itself an improvement over the prior art, even without the configuration of the various areas of the artificial limb casing with different degrees of hardness. The above comments on the artificial limb casing can also be applied to configurations with a textile intermediate layer in which different degrees of hardness have not been used.

The method according to the invention for producing an artificial limb casing provides that a textile intermediate layer is applied to the outer side of a hollow elastomer substrate, which has the form of a natural body limb, and a silicone layer is applied to said intermediate layer. This textile intermediate layer improves the adhesiveness of the silicone coating on the substrate material. In addition, the textile intermediate layer can reduce the tear propagation propensity, so that altogether a greater strength and durability of the artificial limb casing is achieved. A fleece, flock or velour layer may be applied in particular as the intermediate layer. The configuration as a fleece or velour layer has the advantage that there is no woven or knitted structure in the intermediate layer, so that the elasticity of the material is not restricted; this is of advantage in particular in the region of the insertion opening.

The textile intermediate layer is connected in an interlocking manner to the silicone layer and the elastomer substrate, so that even when materials that do not adhere to one another are used a secure connection is achieved between the substrate material and the silicone layer.

The elastomer substrate may be formed from a polyurethane, to the outer side of which the textile layer is applied.

An exemplary embodiment of the invention is explained in more detail below on the basis of the accompanying figures, in which:

FIG. 1 shows a foot casing in side view;

FIG. 2 shows a foot casing in a perspective oblique plan view;

FIG. 3 shows a foot casing in plan view;

FIG. 4 shows a variant of the invention with a silicone coating; and

FIG. 5 shows a foot casing on a lower leg prosthesis.

In FIG. 1, an artificial limb casing 1 is represented, in the form of a foot casing having an end area 2, configured as a sole area, and a joint area 3, configured as an ankle area. Formed within the foot casing 1 is a cavity (not represented), in which a prosthetic foot (likewise not represented) is inserted. Insertion takes place through the insertion opening 4 formed at the upper end. Connected to the insertion opening 4 is the ankle area 3, which in the embodiment represented has a concertina structure 5, which extends above and below an ankle joint axis. The prosthetic foot can be pivoted about this axis, the position of which is represented in FIG. 1 as a round area, for example in order to set the heel height when the wearer of the prosthesis changes to a style of shoe that has a different heel height than the previous shoe.

The ankle area 3 has a material hardness of 15 to 25 Shore A, while the sole area 2 integrally connected thereto has a material hardness of between 45 and 75 Shore A. The transition of the respective Shore hardness from the ankle area 3 to the sole area 2 may be continuous or discrete, for example in a number of stages, so that the greatest hardness is obtained in the lower sole area; connected thereto is an area with a somewhat lower Shore hardness, whereas the lowest Shore hardness is set in the ankle area 3 and in particular in the region of the insertion opening 4.

Over the range of the longitudinal extent of the sole area 2, different material thicknesses may be formed in different areas. To improve the durability, a greater material thickness of the elastomer material, for example polyurethane, may be provided in the heel area 21 than in the mid-foot area; the same applies to the ball area 22 or the toe area 23, which likewise count among the more highly stressed areas of the foot casing 1.

In FIG. 2, the concertina area 5 around the ankle axis can be clearly seen in the perspective representation. It can likewise be seen that a sealing ring 6 that ensures secure sealing with respect to ingress of moisture has been introduced in the insertion opening 4 in the upper area. The sealing ring 6 may either be integrally formed or placed in a recess. Since the ankle area 3 extends beyond the ankle axis in the direction of a lower leg part, the sealing ring 6 lies against a lower leg part and prevents ingress of dirt and moisture from above.

In the plan view according to FIG. 3, the various sole areas, namely the heel area 21, the ball area 22 and the toe area 23, can be seen. It can likewise be seen that, in the exemplary embodiment represented, a greater material thickness is formed in the heel area 21 than in the mid-foot area. The shaping of the foot casing corresponds to that of a natural foot, apart from the fact that only the big toe is individually formed, while the other toes are formed as a contiguous toe arrangement.

In FIG. 4, a variant of the invention in which a fleece layer 8 has been applied as a textile intermediate layer to the polyurethane substrate 9 of the foot casing, as it is shown in FIGS. 1 to 3, is shown in various views, for example at the top left in a schematic cross-sectional view. This textile intermediate layer 8 is connected to the polyurethane material of the foot casing 1, either by way of an adhesive connection or by way of an interlocking embedding in the polyurethane material. In the exemplary embodiment represented, the textile intermediate layer 8 extends only up to the lower area of the concertina area 5. Applied on the outer side of the textile intermediate layer 8 is a silicone layer 7, which has a skin-like texture and represents the outer termination of the foot casing 1. The silicone outer layer 7 is connected in an interlocking manner to the textile intermediate layer 8, so that components which without the textile intermediate layer 8 would not adhere to one another can also be permanently joined to one another. The silicone layer 7 forms the outer termination of the foot casing 1, since it closely resembles a skin-like structure and feel. A disadvantage of a silicone layer 7 on the outer side is the fact that it has only a low tear propagation resistance. The required tear propagation resistance is provided by the polyurethane substrate 9. In addition, the textile intermediate layer 8 further reduces the tear propagation propensity.

In the exemplary embodiment represented, the silicone layer 7 is adhesively attached on the polyurethane substrate 9. For this purpose, the silicone coating is produced separately and connected to the textile intermediate layer 8, for example a fleece layer, by way of an adhesive bond. For this purpose, the textile-covered artificial limb casing is brushed or sprayed with a silicone adhesive or wetted with it in some other way, for example by immersion; the silicone layer 7 is subsequently rolled over or drawn over. Alternatively, the silicone layer 7 may be applied in a silicone bath. Generally provided as the bonding agent between the textile intermediate layer 8 and the silicone layer 7 or the silicone adhesive are liquid silicones, wherein the application of the bonding agent may take place in an immersion bath. The bonding agents enter into an interlocking connection with the textile intermediate layer 8 and a material-bonding connection with the silicone layer 7.

In FIG. 5, a ready-fitted foot casing 1 on a lower leg shaft 10 is shown. The lower leg shaft 10 is likewise provided with a cosmetic covering, which corresponds in the visual look to the foot casing 1. With preference, the cosmetic outer casing of the lower leg shaft 10 is formed from a silicone material; other materials are likewise possible. A substantially seamless transition between the foot casing 1 and the lower leg cosmetic covering 10 is provided. If the heel height of the lower leg prosthesis is changed, compensation can easily take place by way of the concertina structure 5, without compressions or high tensile stresses occurring in the cosmetic foot covering 1.

The foot covering 1 according to the invention has not only the very good technical properties as a result of the polyurethane substrate 9 but also very good visual properties, since the cosmetic foot covering is securely held on the foot casing 1 by the silicone coating 7 and as a result does not form any folds.

Insofar as the textile intermediate layer 8 is not formed as a woven or knitted structure, the elasticity of the foot casing 1 is not restricted. In addition, the fleece or velour covering already allows a coloring that can serve as a base for the silicone layer 7. The textile layer 8 provides a uniform application of adhesive.

The textile layer 8 is applied after the production or during the production of the polyurethane substrate 9, for example by a fleece material being placed into the negative mold of the foot blank. Then, the polyurethane material is filled into the mold and cured. After removing the blank, the silicone layer 7 may then be applied as a terminating layer, for example by impregnating in a silicone bath or the like.

The invention claimed is:

1. An artificial limb casing, comprising:
an insertion opening for inserting the artificial limb, wherein a joint area to which an end area is integrally connected is formed on the casing, the joint area being arranged in alignment with a joint of the artificial limb, the end area being arranged distal of the joint area along a length of the artificial limb casing, and the casing is formed from an elastomer material that has a lower Shore hardness in the joint area than in the end area, the elastomer material comprising polyurethane, wherein there is a lower material thickness in the joint area than in the end area.

2. The artificial limb casing as claimed in claim 1, wherein the casing is a foot casing, the end area of which is formed as a sole area and the joint area of which has a lower Shore hardness than the sole area.

3. The artificial limb casing as claimed in claim 2, wherein the sole area has a heel area, a ball area and a toe area and a material reinforcement in the sole area is formed in at least one of the heel area, ball area and toe area.

4. The artificial limb casing as claimed in claim 1, wherein the elastomer material has a hardness of 15 to 25 Shore A in the joint area.

5. The artificial limb casing as claimed in claim 1, wherein the elastomer material has a hardness of 45 to 75 Shore A in the end area.

6. The artificial limb casing as claimed in claim 1, wherein the elastomer material has a uniform hardness in the end area.

7. The artificial limb casing as claimed in claim 1, wherein the hardness of the elastomer material decreases continuously from the end area to the joint area.

8. The artificial limb casing as claimed in claim 1, wherein a silicone coating is applied on an outer side of the elastomer material.

9. The artificial limb casing as claimed in claim 8, wherein a textile intermediate layer is arranged between the silicone coating and the elastomer material.

10. The artificial limb casing as claimed in claim 9, wherein the textile intermediate layer is formed as a fleece, velour or flock layer.

11. A method for producing an artificial limb casing, comprising:
  applying a textile intermediate layer to an outer side of a hollow elastomer substrate;
  applying a silicone layer to said textile intermediate layer opposite the hollow elastomeric substrate, the silicone layer providing at least one of an improved tactile feel and an improved visual effect;
  wherein the textile intermediate layer improves adhesion of the silicone layer to the hollow elastomeric substrate.

12. The method as claimed in claim 11, wherein the elastomer substrate is formed as a polyurethane substrate and the textile intermediate layer is applied to the outer side of the hollow polyurethane substrate and the silicone layer is applied to said intermediate layer.

13. The method as claimed in claim 11, wherein a fleece, flock or velour layer is applied as the intermediate layer.

14. The method as claimed in claim 11, wherein the textile intermediate layer is connected in an interlocking manner to the silicone layer and the hollow elastomeric substrate.

15. An artificial limb casing, comprising:
  an insertion opening for inserting the artificial limb, wherein a joint area to which an end area is integrally connected is formed on the casing, the joint area being arranged in alignment with a joint of the artificial limb, the end area being arranged distal of the joint area along a length of the artificial limb casing, and the casing is formed from an elastomer material that has a lower Shore hardness in the joint area than in the end area, wherein an accordion-shaped concertina structure is formed in the joint area.

16. The artificial limb casing of claim 15, wherein there is a lower material thickness in the joint area than in the end area.

17. An artificial limb casing, comprising
  an insertion opening for inserting the artificial limb, wherein a joint area to which an end area is integrally connected is formed on the casing, the joint area being arranged in alignment with a joint of the artificial limb, the end area being arranged distal of the joint area along a length of the artificial limb casing, and the casing is formed from an elastomer material that has a lower Shore hardness in the joint area than in the end area, wherein there is a lower material thickness in the joint area than in the end area.

18. An artificial limb casing, comprising:
  an insertion opening for inserting the artificial limb, wherein a joint area to which an end area is integrally connected is formed on the casing, the joint area being arranged in alignment with a joint of the artificial limb, the end area being arranged distal of the joint area along a length of the artificial limb casing, and the casing is formed from an elastomer material that has a lower Shore hardness in the joint area than in the end area, wherein the casing includes zonings of at least one of different material thicknesses, material hardnesses, or colorations, and there is a lower material thickness in the joint area than in the end area.

19. An artificial limb casing, comprising
  an insertion opening for inserting the artificial limb, wherein a joint area to which an end area is integrally connected is formed on the casing, the joint area being arranged in alignment with a joint of the artificial limb, the end area being arranged distal of the joint area along a length of the artificial limb casing, and the casing is formed from an elastomer material that has a lower Shore hardness in the joint area than in the end area, wherein a sealing ring is embedded in the insertion opening, and there is a lower material thickness in the joint area than in the end area.

* * * * *